United States Patent [19]

Montecalvo et al.

[11] Patent Number: 5,522,878
[45] Date of Patent: Jun. 4, 1996

[54] SOLID MULTIPURPOSE ULTRASONIC BIOMEDICAL COUPLANT GEL IN SHEET FORM AND METHOD

[75] Inventors: David A. Montecalvo, Plymouth; David Rolf, Minneapolis, both of Minn.

[73] Assignee: LecTec Corporation, Minnetonka, Minn.

[21] Appl. No.: 54,745

[22] Filed: Apr. 26, 1993

Related U.S. Application Data

[63] Continuation-in-part of Ser. No. 344,698, Apr. 28, 1989, Pat. No. 5,205,297, which is a continuation-in-part of Ser. No. 173,589, Mar. 25, 1988, abandoned.

[51] Int. Cl.⁶ .......................................................... A61B 8/00
[52] U.S. Cl. ................................................ 607/152; 73/644
[58] Field of Search ........................ 128/24 AA, 639–641, 128/662.03, 663.01; 607/152, 97; 604/20; 73/644; 252/500; 601/2

[56] References Cited

U.S. PATENT DOCUMENTS

| | | | |
|---|---|---|---|
| 4,002,221 | 1/1977 | Buchalter | 181/0.5 |
| 4,089,329 | 5/1978 | Couvillon, Jr. et al. | 128/2 T |
| 4,125,110 | 11/1978 | Hymes | 128/2.06 E |
| 4,270,832 | 6/1981 | Tanabe | 339/105 |
| 4,274,420 | 6/1981 | Hymes | 128/641 |
| 4,299,231 | 11/1981 | Karmann et al. | 128/639 |
| 4,301,805 | 11/1981 | Peers-Trevarton | 128/419 |
| 4,349,030 | 9/1982 | Belgard et al. | 128/419 |
| 4,365,516 | 12/1982 | Molina | 73/644 |
| 4,458,696 | 7/1984 | Larimore | 128/798 |
| 4,459,854 | 7/1984 | Richardson et al. | 73/644 |
| 4,474,570 | 10/1984 | Ariura et al. | 604/20 |
| 4,515,162 | 5/1985 | Yamamoto et al. | 128/643 |
| 4,528,652 | 7/1985 | Horner et al. | 367/162 |
| 4,539,996 | 9/1985 | Engel | 128/640 |
| 4,556,066 | 12/1985 | Semrow | 128/639 |
| 4,577,643 | 3/1986 | Beranek | 128/785 |

(List continued on next page.)

FOREIGN PATENT DOCUMENTS

| | | | |
|---|---|---|---|
| 2552611 | 9/1983 | France | H04R 1/46 |
| 61-120053 | 8/1984 | Japan | G01N 27/30 |
| 3254730 | 2/1990 | Japan | A61B 5/02 |
| 1546900A | 1/1986 | U.S.S.R. | G01N 29/00 |
| 2045088 | 10/1980 | United Kingdom | A61B 5/04 |
| WO81/00785 | 3/1981 | WIPO | H01B 9/06 |

OTHER PUBLICATIONS

"Peripheral Vascular Noninvasive Measurements" *Encyclopedia of Medical Devices and Instrumentation*, J. Webster (Ed.); Wiley & Sons New York, 1988, pp. 2220–2238.
*Introduction to Biomedical Equipment Technology*. Carr and Brown; John Wiley & Sons, New York. pp. 294–298.

*Primary Examiner*—Krista M. Zele
*Assistant Examiner*—Brian L. Casler
*Attorney, Agent, or Firm*—James V. Harmon

[57] ABSTRACT

A solid, multipurpose, flexible, ultrasonic biomedical couplant hydrogel in sheet form is applied to the skin of a patient to facilitate the transfer of ultrasound energy between a standard ultrasound instrument and the body. The couplant sheet has broad upper and lower surfaces and a narrow peripheral edge which is usually circular, square or rectangular but can have other shapes such as the shape of the part of the body being monitored. During use, the lower surface of the sheet is applied to the skin of a patient and remain in place throughout use. The ultrasound instrument is then passed back and forth, usually in contact with the exposed upper surface of the hydrogel sheet while ultrasound energy is transmitted through the hydrogel which serves as a transmission path for the sonic energy passing to and from the body of the patient. The hydrogel sheet of the present invention is a flexible, self-supporting solid sheet which holds its form during storage and when placed on the body. The sheet contains water and a humectant such as triethylene glycol or glycerin and a network of long hydrophilic polymer molecules that hold the liquid in place and give solidity to the hydrogel sheet The polymer can comprise polyacrylamide, karaya gum or a modified starch.

23 Claims, 4 Drawing Sheets

U.S. PATENT DOCUMENTS

| | | | |
|---|---|---|---|
| 4,674,512 | 6/1987 | Rolf | 128/640 |
| 4,675,009 | 6/1987 | Hymes et al. | 604/304 |
| 4,692,273 | 9/1987 | Lawrence | 128/640 |
| 4,694,835 | 9/1987 | Strand | 128/640 |
| 4,699,146 | 10/1987 | Sieverding | 128/640 |
| 4,702,732 | 10/1987 | Powers et al. | 604/20 |
| 4,706,680 | 11/1987 | Keusch et al. | 128/640 |
| 4,717,378 | 1/1988 | Perrault et al. | 604/20 |
| 4,785,822 | 11/1988 | Wallace | 128/675 |
| 4,825,876 | 5/1989 | Beard | 128/675 |
| 4,920,972 | 5/1990 | Frank et al. | 128/675 |
| 4,989,607 | 2/1991 | Keusch et al. | 607/152 |
| 5,002,792 | 3/1991 | Vegoe | 128/639 |
| 5,036,857 | 8/1991 | Semmlow et al. | 128/715 |
| 5,109,863 | 5/1992 | Semmlow et al. | 128/715 |
| 5,123,423 | 6/1992 | Scharnberg | 607/152 |
| 5,125,405 | 6/1992 | Schmid | 128/639 |

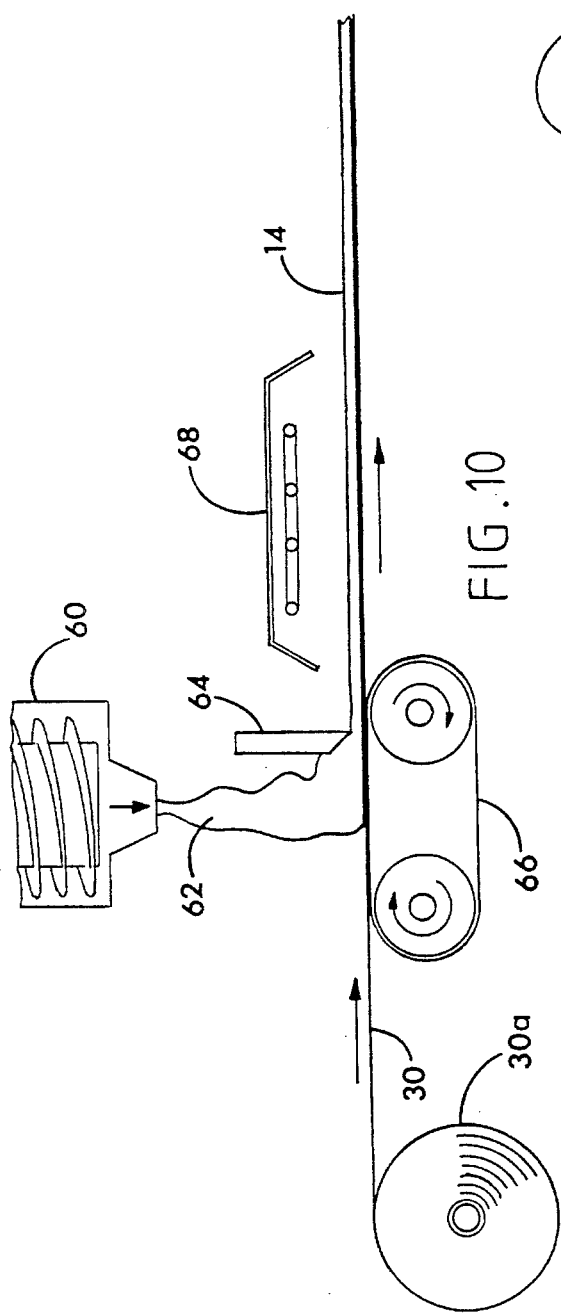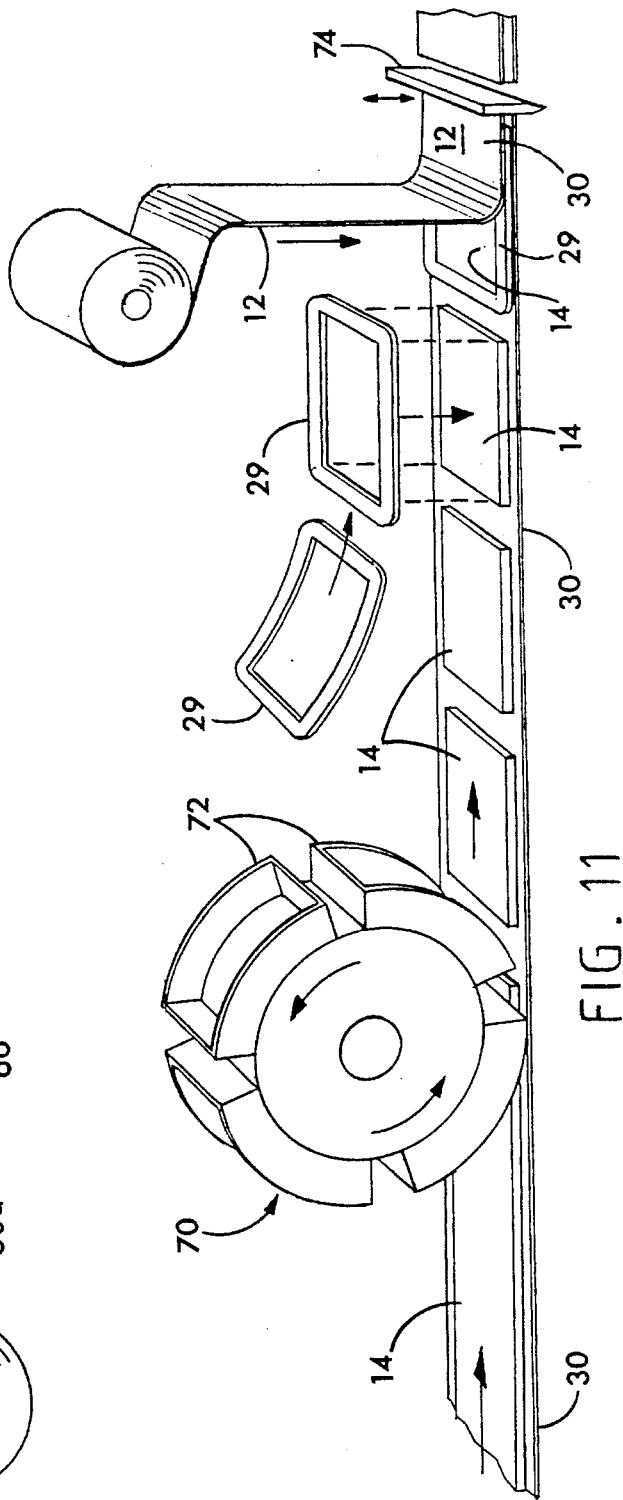

SOLID MULTIPURPOSE ULTRASONIC BIOMEDICAL COUPLANT GEL IN SHEET FORM AND METHOD

This application is a continuation-in-part of U.S. application Ser. No. 07/344,698, filed Apr. 28, 1989, now U.S. Pat. No. 5,205,297, which was a continuation-in-part of U.S. application Ser. No. 173,589 filed Mar. 25, 1988 (abandoned).

FIELD OF THE INVENTION

The present invention relates to biomedical devices and more particularly to an externally applied multipurpose solid ultrasonic couplant gel and method for transferring ultrasonic vibrations to and from a patient.

BACKGROUND OF THE INVENTION

Ultrasonic diagnostic devices have been used increasingly in recent years, particularly for fetal monitoring and for measuring blood flow (plethysmography). Substances currently used as a couplant material to facilitate transfer of ultrasonic energy to the patient have not been entirely satisfactory. A liquid gel has, for example, been used in the past for ultrasonic procedures. This gel is an amorphous fluid which can be squeezed from a collapsible tube and then applied to the patient by smearing it onto the skin. These fluids are messy and perceived as being cold by the patient. They also require cleanup following use. In addition, if left on the skin for a period of time, they can dry out. Moreover, the thickness of the fluid film applied to the skin is non-uniform. It is believed that this contributes to inconsistencies in the signals received by the ultrasound transducer. For example, when a Doppler wand is used in ultrasound diagnostics, it appears to be differences in the fluid film from one area to another that cause occasional sudden bursts of noise in the signal received. When the operator is using earphones to listen to the Doppler signal being received, artifacts in the signal being received sound like sudden blasts of loud static which is, of course, very objectionable.

One example of a liquid gel is in U.S. Pat. No. 4,002,221 which describes a transducer coupling agent in the form of a gel having a viscosity similar to mayonnaise and formed from copolymers of methylvinyl ether and maleic acid and carboxy polymethylene polymer with alkali metal salts as thickeners. U.S. Pat. No. 4,459,854 describes an ultrasonic transducer coupling member composed of a hydrogel which fits into an opening between interconnected walls that define a generally trapezoidal space for the hyrodgel. The hydrogel is placed in the trapezoidal space. The hydrogel can be a copolymer of vinyl pyrrolidone and phenolethyl methacrylate. Silicone fluid has also been used, but silicones are dielectrics and electrical insulators. In addition, the density of silicone is not the same as that of the body. These factors can interfere with the transfer of electrical and/or sonic energy to and from the body.

It is a general object of the present invention to provide an improved ultrasonic couplant gel which is easily applied to the body and removed, which is flexible and self-supporting, and which conforms readily to the contours of the body and preferably has at least a moderately tacky lower surface to form a mechanical bond with the skin but which can be easily removed later, which is uniform in thickness, facilitates movement of the ultrasound instrument in all directions thereacross, does not tend to contribute to signal noise and will efficiently transmit ultrasonic energy to and from the body. In addition, it is an object to provide a couplant gel which is easy to handle, can be quickly applied to the body by medical personnel and confined to an area of the body having a predetermined perimeter. It is a more specific object to provide a solid couplant gel in sheet form which is suited for various ultrasound application such as fetal monitoring during pregnancy as well a peripheral vascular non-invasive ultrasound measurements which may utilize pulsed Doppler instrumentation to detect blood flow at a specific distance from the ultrasonic probe and for other biomedical applications.

These and other more detailed and specific objects of the present invention will be better understood by reference to the following brief summary which describes by way of example but a few of the various forms of the invention within the scope of the appended claims.

SUMMARY OF THE INVENTION

The present invention provides a solid, multipurpose, flexible ultrasonic biomedical couplant hydrogel in sheet form. The couplant sheet has broad upper and lower spaced apart top and bottom surfaces and a narrow periphery which is usually circular, square or rectangular but can have other shapes such as the shape of the part of the body being monitored. During use, the lower surface of the sheet is applied to the skin of a patient and remains in place throughout use. The ultrasound instrument is then passed back and forth, usually in contact with the exposed upper surface of the gel sheet while ultrasound energy is transmitted through the gel which serves as a transmission path for the sonic energy passing to and from the body of the patient. Instead of being an amorphous fluid, the gel sheet of the present invention is a flexible, self-supporting solid sheet which holds its form during storage and when placed on the body. It consists of two major components: a liquid and a network of long polymer molecules that hold the liquid in place and give the gel a degree of solidity. By contrast, in a fluid gel there is only enough friction between the polymer molecules to hinder rapid flow, causing the fluid to be thick and viscous. At higher concentrations, the polymer coils intertwine so as to give the gel visco-elastic properties but will still allow a gel to flow enough so that it can be smeared over the skin with the fingers or a spatula and leaves a residue that requires cleanup following use. On the other hand, in the present invention the gel is sufficiently "set" so that the dispersion of the polymer strands behaves more as a flexible solid rather than flowing when manipulated. For example, the gel of the present invention has a particular shape and retains that shape even after being placed on the body. Moreover, if perturbed mechanically, it will eventually separate along a fracture line or it can be torn when pulled apart by hand. It is flexible, somewhat elastic, conforms easily to the body contours, and is preferably somewhat tacky, at least on the lower surface so as to establish a mechanical connection or bond with the skin to enhance the transfer of ultrasound energy but leaves no residue and requires no cleanup.

The sheet includes a solid phase comprising a natural or synthetic hydrophilic polymer which is dispersed in a liquid phase to provide the flexible, solid hydrogel matrix. The liquid phase of the matrix preferably includes water together with a hydrophilic humectant such as a polyhydric alcohol, i.e., one having two or more hydroxyl groups.

Optionally, in one preferred form of the invention, a minor amount of a gelation inhibitor is included in an amount sufficient to reduce the viscosity of the matrix as it is being formed into a sheet to prevent premature gelation, i.e., setting of the matrix structure prior to conversion into sheet form as, for example, by the application of the hydrogel as it is being formed to a backing or supporting sheet. In one preferred forming process the hydrogel is made by coating it while still formable onto a flexible backing sheet, i.e., a liner sheet, usually paper or plastic film. Flexible liner sheets are preferably provided on both the upper and lower surfaces of the hydrogel sheet. The liner sheets, which enclose the gel sheet and also keep it clean during shipment and storage are usually weakly bonded to the upper and lower surface of the gel so that they can be removed prior to use. The exposed lower surface of the hydrogel sheet contacts the body of a patient directly during use and preferably forms a removable bond with the skin.

The hydrogel sheet of the present invention functions as an interface between the ultrasound device as it emits the ultrasound waves and the skin. The hydrogel sheet transmits bursts of ultrasound energy to the target and also transmits portions of the energy back to the receiver contained in the ultrasound device.

The hydrogel sheet of the present invention can be used, for example, in procedures for monitoring fetal activity and movement (as in transabdominal Doppler ultrasound) as well as the measurement of peripheral vascular disease and Doppler echocardiography. A patch of the gel sheet can be applied to a patient and used repeatedly, i.e., the sheet is reusable and will remain attached to the skin between periods of use. The sheet can also be provided with a feature which enables it to resist moisture gain or loss either prior to or during use.

The ultrasonic couplant sheets of the present invention are substantially uniform in thickness and remain so throughout use as they efficiently transfer sonic energy to and from the body of the patient. They are easy to apply and use; they are supple, pliable, soft will conform to the skin contours. If desired, either the upper or lower surface, or both, can be easily moistened with water or otherwise lubricated just prior to or during use. They are non-irritating, have no odor and are safe to use. They also preferably cling to the skin and thus remain in place on the skin during use, but afterwards can be easily removed and require little, if any, cleanup.

Additional features of the invention will be apparent from consideration of the accompanying specification, claims and drawings which illustrate by way of example but a few of the various ways in which the invention can be accomplished.

THE FIGURES

FIG. 10 is a semi-diagrammatic side elevational view showing the formation of the gel sheet; and FIG. 11 is a semi-diagrammatic perspective view showing assembly of one form of ultrasonic couplant device in accordance with the invention.

DETAILED DESCRIPTION OF THE INVENTION

Figure 1:
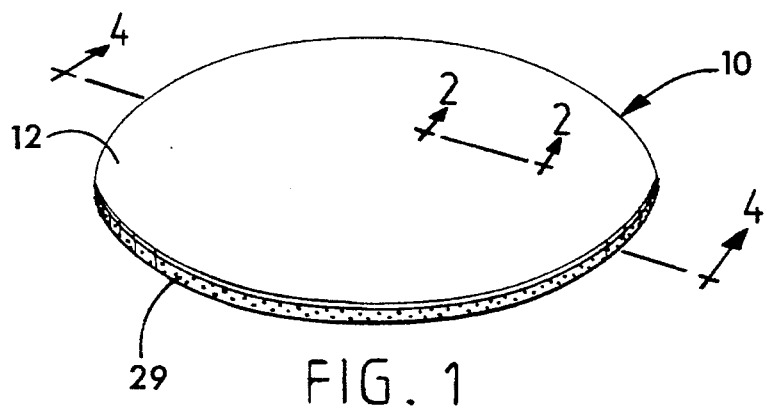
FIG. 1 is a perspective view of one form of the invention.

A solid but flexible gel sheet is provided for transferring (coupling) ultrasonic energy to the body. The sheet is composed of a solid phase comprising a synthetic or natural hydrocolloid, such as polyacrylamide or polysaccharide, e.g., a polysaccharide gum or a mixture thereof together with a liquid phase comprising a hydrating agent, e.g., a polyhydric alcohol and water. By the term polyhydric alcohol is meant an alcohol with two or more hydroxyl groups.

The hydrogel sheet has an exposed skin-contacting surface which is preferably sufficiently tacky to bond to the skin for enhancing the transmission of the ultrasonic signal to the body. The hydrogel sheet moreover is stable and self-supporting when applied, i.e., it is nonfluid and although flexible will not flow appreciably during storage or after being applied to the patient's skin. In a preferred form of the invention, the hydrocolloidal mass that makes up the sheet possesses adhesive properties, at least on its lower surface for bonding the sheet to the skin, but the top surface need not have adhesive properties and, if desired, can be covered with a thin membrane to reduce moisture loss.

The solid phase of the coupling sheet most preferably comprises about 10% to about 40% by weight of a hydrophilic synthetic and/or hydrophilic natural or synthetic polysaccharide such as a polysaccharide gum. The matrix may include synthetic polymers such as polyacrylamide, polyacrylic acid and its salts, poly maleic anhydride, polyvinyl pyrrolidone and its salts, or a modified starch such as pregelatinized starch. Of the naturally occurring gums which may be used are gum karaya, gum acacia, locust bean gum as well as other polysaccharide gums. Synthetically modified gums such as modified guar gums and synthetically modified celluloses are also suitable. The synthetic polymers and/or synthetic or natural gums or other polysaccharide constitute the solid dispersed phase of the hydrogel sheet. The liquid phase includes a humectant such as a polyhydric alcohol, e.g., glycerin, triethylene glycol, or propylene glycol or a mixture thereof, and water for hydrating the solid phase. The liquid phase most preferably comprises about 10% to 70% by weight of the hydrogel sheet. It is preferred that the polyhydric alcohol be present in the amount of about 10% to 15% by weight of the sheet and the water is preferably present in an amount of approximately 1% to about 70% by weight of the hydrogel sheet. All quantities herein, unless otherwise stated, are expressed as parts or percent by weight of the hydrogel sheet.

The thickness of the finished hydrogel sheet is preferably from about 10 mils to 100 mils. A sheet of 80 mils thickness is typical. The sheet can be of any suitable dimensions e.g., 3 inches by 5 inches or 8 inches by 10 inches (for fetal monitoring), and the sheet can be enclosed within a frame or border in some applications as will be described herein below. In other applications, the hydrogel sheet is provided without a border. After being applied to the skin, body moisture as well as body salts and heat are absorbed by the sheet. This tends to increase the tackiness of its lower surface. In some embodiments of the present invention, the bond to the skin and elastic properties of the hydrogel sheet tend to be enhanced as the contact time with the skin increases.

The polyhydric alcohol swells the hydrophilic polymer and is involved in hydrogen bonding and cross-linking of the polymer. If too much is added, the hydrogel matrix tends to become soft or mushy in nature. However, if too little is added, the matrix tends to be hard and dry. Triethylene glycol is more fluid but a less effective hydrating substance than glycerin.

The amount of hydrophilic polysaccharide gum and/or hydrophilic synthetic polymer can be varied from about 10% to about 40% by weight of the matrix. This material used in increasing amounts builds viscosity and elasticity of the mixture. Excessive amounts cause the formulation to become too elastic or tough to be spread evenly into a sheet. However, if too little is used the matrix may become too soft or runny.

Water is preferably present in an amount of between about 10% to about 70% by weight of the matrix for the purpose of swelling the hydrophilic polymer. Too much water tends to make the product too soft. If not enough water is present in the formulation, the product may be hard, dry and not tacky enough to adhere to the skin.

The previously mentioned components are combined in the following manner. The humectant, e.g., triethylene glycol, is first mixed with the hydrophilic polymer to assure that the polymer is wetted and the mixture is homogenous. This mixture is then combined with the most polar liquids such as glycerin and water. This process is preferably completed by continuous mixing rather than by batch mixing since the viscosity of the mixture builds up rapidly with respect to time of mixing. The liquid components are preferably chilled, e.g., to between about −25° C. and +25° C. This helps to decrease the rate of viscosity increase.

If desired, a gelation inhibitor, e.g., a salt of a weak acid such as $Mg(OAc)_2$, can be added to the mixture for stabilizing the viscosity by decreasing the rate at which viscosity increases in the hydrocolloidal mass. A preferred method of forming the hydrogel sheet will be described in more detail below with reference to FIGS. 10 and 11. After mixing until homogenous, the mixture is coated onto a backing and is then cured by heating it briefly, e.g., to about 100° F. When $Mg(OAc)_2$ is used, it is preferably present in an amount of from about 2% to about 12% by weight and preferably in an amount of from about 6% to 9% by weight. Increasing the amount of $Mg(OAc)_2$ decreases the viscosity building rate of the hydrogel matrix during the mixing procedure just prior to the application of the coating to the backing. Too great an amount will unduly inhibit viscosity increase and too small an amount will allow the gel to thicken so quickly that spreading may become difficult.

Viscosity buildup is also controlled by the mixing temperature. Typically, during mixing the dispersion is chilled to about −5° C. to about +10° C. At this temperature, about one minute is allowed to coat the hydrogel matrix sheet onto a backing such as a sheet of paper or plastic. The matrix preferably enters the coater at a temperature of about −25° C. to about +20° C. and most preferably from about −15° C. to about +5° C.

Refer now to the figures and particularly to FIGS. 1–4 which illustrate a couplant device 10 embodying the invention which in this case is circular. The circular couplant device 10 includes an upper removable protective flexible layer 12 formed, for example, from a sheet of siliconized paper or plastic, e.g., 5 mil polyethylene film. Positioned in contact with the lower surface of the protective layer 12 is a sheet or patch of flexible hydrogel material 14 having a composition as described above. The hydrogel sheet 14 in this case is circular and has a lower surface 16 which is exposed just prior to use and is preferably slightly tacky so that it will form a removable mechanical bond to the surface of the skin 18 (FIG. 2) after being applied.

Figure 2:
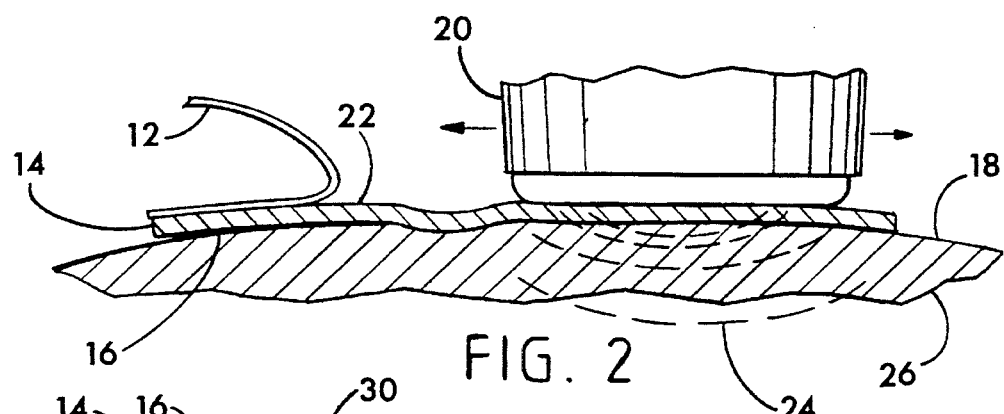
FIG. 2 is a partial vertical sectional view taken on line 2—2 of FIG. 1 showing the couplant gel in use.
Figure 3:
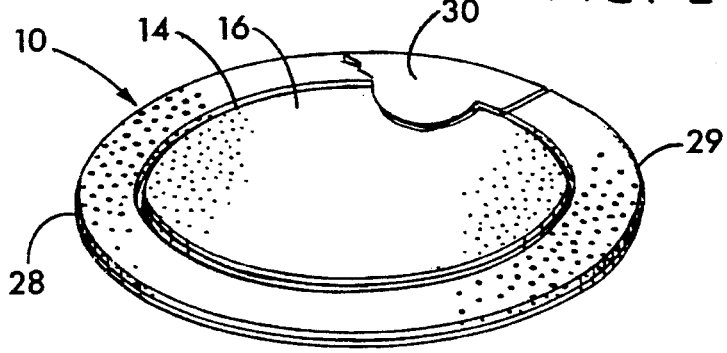
FIG. 3 is a bottom perspective view of FIG. 1.

It will be seen especially in FIG. 2 that the sheet of flexible hydrogel material 14 is substantially uniform in thickness throughout so that during use after the protective layer 12 e.g., plastic film, has been removed, a standard ultrasound instrument 20 (FIG. 2) can be placed in contact with the upper surface 22 of the hydrogel sheet 14 and slid back and forth wherever desired by the healthcare professional, causing ultrasound waves 24 to be passed into the body 26 and then received by the ultrasound instrument 20 from the body of the patient. The hydrogel sheet 14 is enclosed, i.e., surrounded with a frame or border 29, preferably formed from a sheet of plastic foam such as foamed polyurethane, polyethylene, or foamed rubber, etc. with a layer of adhesive 28, preferably a pressure-sensitive adhesive, applied to its lower surface. The couplant device 10 also includes a second removable protective layer 30 (only a portion of which is shown in FIG. 3) applied to the lower surface 16 of hydrogel sheet 14 and to the adhesive layer 28 of the border 29.

Figure 4:
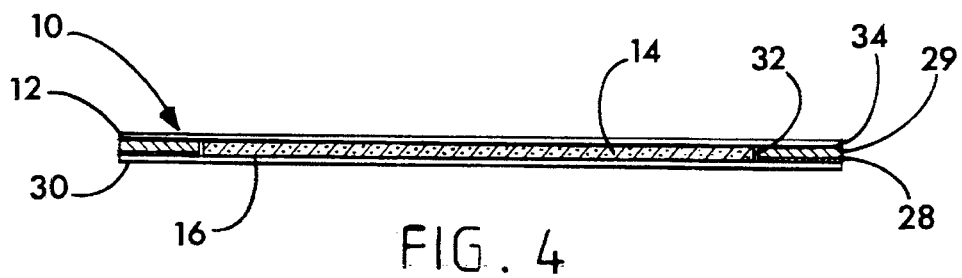
FIG. 4 is a vertical sectional view taken on line 4—4 of FIG. 1.

FIG. 4 shows the couplant device 10 prior to use with both of the removable protective layers 12 and 30 in place. To use the couplant device 10, the lower protective layer 30 is removed first. The couplant device 10 is then applied to the skin. As this is done, the adhesive 28 will form a bond with the skin as will the tacky lower surface 16 of the hydrogel sheet 14. The couplant device 10 of the present invention can be used in that condition, but it is preferably placed in use after removing the upper protective layer 12 as shown in FIG. 2. As already mentioned, the ultrasound instrument 20 is then placed in contact with the broad upper surface 22 of the hyrodgel sheet 14 and slid in any direction desired while readings are taken.

The hydrogel layer 14 can be of any thickness but is preferably between about 10–100 mils and usually about 80 mils thick. The polyethylene foam ring 29 is about 0.064 inches in thickness. As shown in FIG. 2, the hydrogel sheet 14 is supple, flexible and conforms to the contours of the body 26 during use. It can be kept in place on the body over an extended period of time and used periodically, and can then be removed without the requirement for cleanup simply by lifting one edge and peeling it away from the skin. In hospitals where a reading is taken periodically, e.g., every hour or so, the invention is very advantageous since the hydrogel sheet 14 can be left in place on the skin of the patient throughout the entire period of time that the diagnostic information is taken.

The border 29 completely surrounds the periphery of the hydrogel sheet 14, thus helping to prevent the loss of moisture from the peripheral edge 32 of the hydrogel sheet 14. The top liner sheet 12 can be removably bonded to the border 29 by means of a layer of pressure-sensitive adhesive 34 on the upper surface of the border. This will help to hold the hydrogel sheet 14 more reliably against the skin as well as helping to seal the hydrogel sheet 14 from the environment on all sides so as to reduce moisture loss. If the upper liner sheet 12 is left in place during use, it will act as a membrane for helping to reduce moisture loss from the upper surface 22 of the hydrogel sheet 14.

Figure 4A:
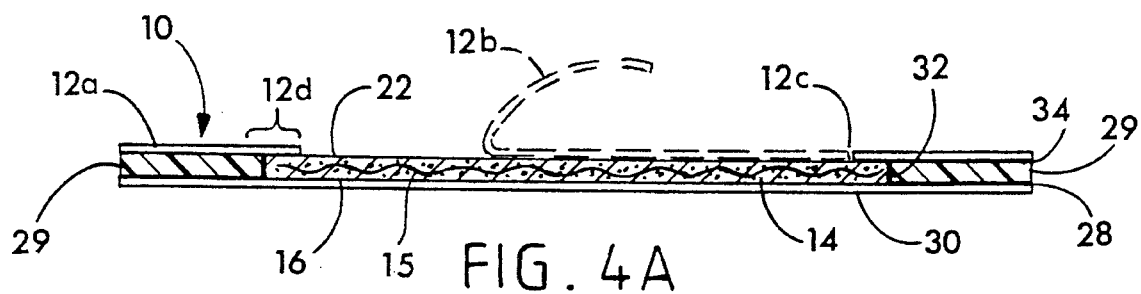
FIG. 4A is a vertical cross-sectional view similar to FIG. 4 of a modified form of the invention.

Refer now to FIG. 4A which illustrates a modified form of the invention. The same numerals refer to corresponding parts in FIGS. 1–4.

As seen in FIG. 4A, the upper liner sheet 12a (which corresponds to the liner sheet 12 of FIGS. 1–4) has a removable center portion 12b formed by making a circular cut 12c in the sheet 12a somewhat smaller in size than the hydrogel sheet 14. When the removable center portion 12b is removed so that the instrument 20 can be placed against the upper surface of the hydrogel sheet 14, a portion 12d of sheet 12a will still overlap and form a bridge between the foam border 29 and the hydrogel sheet 14 to help bond the border 29 hydrogel sheet 14 together. Because the hydrogel sheet 14 is usually tacky on both exposed surfaces, the hydrogel 14 will normally provide a pressure-sensitive bond with the overlapping section 12d of the liner sheet 12a. Optionally, the hydrogel sheet 14 has embedded within it a piece of cloth or scrim 15, e.g., of cotton, nylon or polyester to provide additional strength. As in FIG. 2, the lower liner sheet 30 of FIG. 4A is entirely removed before the couplant device 10 is applied to the skin of the patient.

Figure 5:
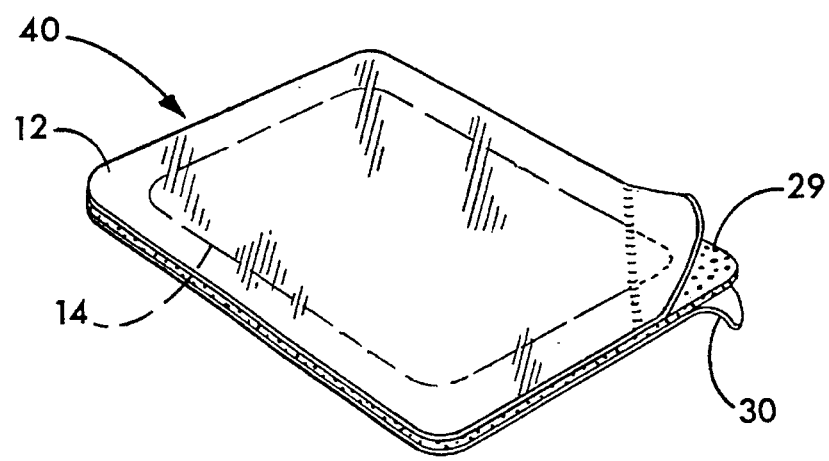
FIG. 5 is a perspective view of another form of the invention having a generally rectangular shape.
Figure 6:
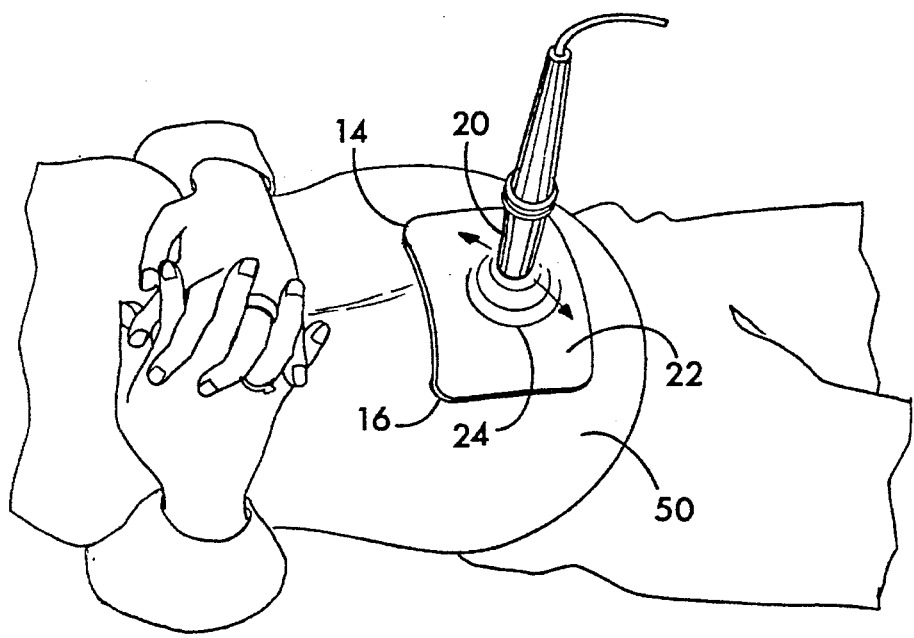
FIG. 6 is a perspective view of another form of couplant gel in accordance with the invention during use in fetal monitoring.

Refer now to FIG. 5 which illustrates another modified form of the invention wherein the same numerals refer to corresponding parts in FIGS. 1–4. The couplant device indicated generally at 40 is in all respects similar to that of FIGS. 1–4 except that it is rectangular in shape rather than circular. It can be used for application to the body as shown in FIGS. 1–4 with the foam 29 remaining in place surrounding the hydrogel sheet 14 or, if desired, the foam border 29 can be removed at the same time that the liner sheets 12 and 30 are removed so that the hydrogel sheet 14 can be placed on the patient without any border, for example as shown in FIG. 6. In FIG. 6, the hydrogel sheet 14 is used for fetal monitoring by placing the hydrogel sheet 14, which in this instance measures about 6 inches by 8 inches, onto the abdomen 50. The surface adhesion of the lower surface 16 of the hydrogel sheet 14 will keep the hydrogel sheet in place on the abdomen 50 during use as the ultrasound instrument 20 is slid back and forth across the upper surface 22 of the hydrogel sheet 14. The natural lubricity of the hydrogel sheet 14 facilitates movement of the instrument 20. Because the hydrogel sheet 14 is uniform in thickness, precise readings can be obtained throughout use. The normally tacky lower surface 16 of the hydrogel sheet 14 establishes good mechanical contact by providing a removable bond with the skin to help enhance the transmission of ultrasound waves 24 to and from the body.

Figure 7:
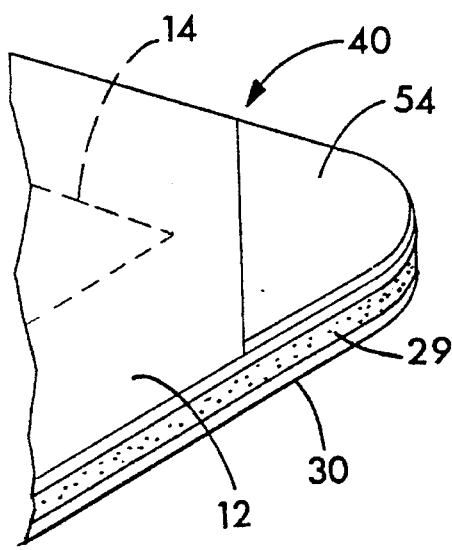
FIG. 7 is a partial view of one corner of the couplant gel showing a liner removal tab.

Refer now to FIG. 7 which illustrates a modified form of the invention shown in FIG. 5. As seen in FIG. 7, one corner of the upper removable liner sheet 12 has bonded to its upper surface a paper tab 54 to help facilitate the removal of the liner 12. The paper tab 54 projects up slightly and thereby helps one get a finger-hold at the corner of the liner sheet 12 so that it can be easily and quickly removed. A similar paper tab (not shown) can also be provided for the lower liner sheet 30 if desired to help facilitate its removal prior to use. For this application, the couplant device 10 can have dimensions of about 2 inches by 3 inches.

Figure 8:
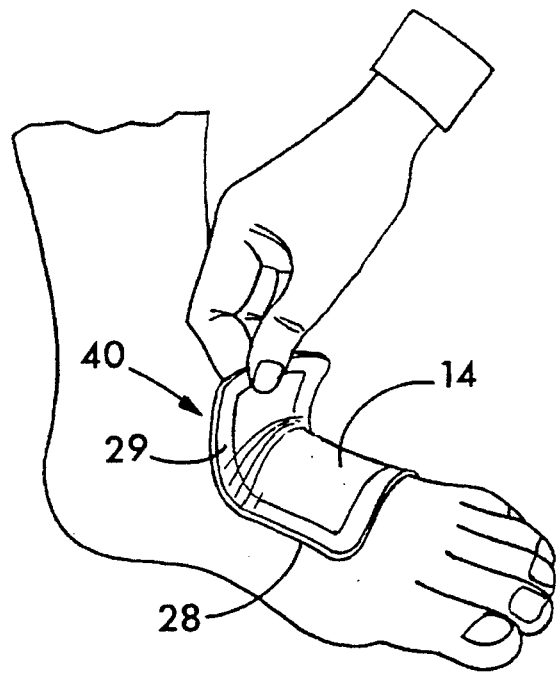
FIG. 8 is a perspective view of the invention being applied for use in peripheral vascular non-invasive ultrasonic blood flow monitoring.
Figure 9:
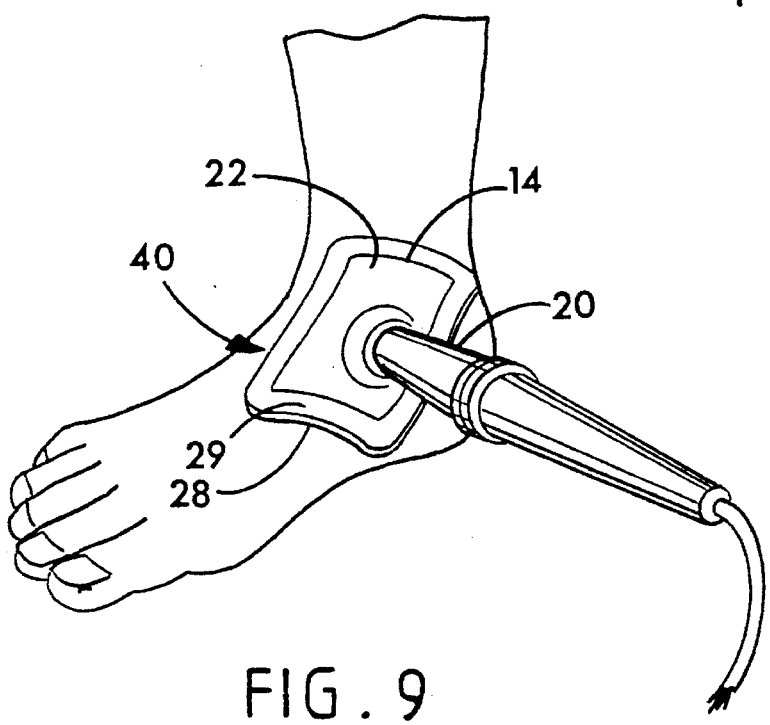
FIG. 9 shows the couplant gel of the invention applied in a different position for blood flow monitoring in a different area.

Refer now to FIGS. 8 and 9 which illustrate the couplant device of the present invention in two different positions for use in peripheral vascular non-invasive ultrasound measurements. In this application, pulsed Doppler instrumentation is used to detect blood flow; that is to say, for plethysmography. In FIG. 8, the flexible hydrogel sheet 14 is shown as it is being applied to the top of the foot. As this is done the bottom surface 16 of the hydrogel sheet 14, as well as the adhesive at 28 on the lower surface of the border or frame 29, forms a bond with the skin to thereby hold the hydrogel sheet 14 in place during use.

When a different blood vessel is used, the couplant device 10 including the hydrogel sheet 14 together with the plastic foam border 29 can be applied to the side of the foot in the ankle area as shown in FIG. 9. The couplant device is held in place by means of the pressure-sensitive layer 28 on the lower surface of the foam border 29 as well as by the tacky lower surface of the hydrogel sheet 14. Once applied, the ultrasound instrument, such as the Doppler ultrasound transducer 20, is placed in contact with the exposed upper surface 22 of the hydrogel sheet 14 to make readings. If desired, the instrument can be slid about on the upper surface 22 of the hydrogel sheet 14 until operation is optimized.

Refer now to FIGS. 10 and 11 which illustrate diagrammatically the formation of the hydrogel sheet 14 and the assembly of the completed couplant device 10 including the border 29.

The components are preferably combined in the following manner. Triethylene glycol or other humectant is first mixed with the hydrophilic natural or synthetic polymer, most preferably within a continuous mixer-extruder 60 to assure that the polymer is wetted and the mixture is homogenous. This mixture is then combined with the most polar of the liquids such as glycerin and water, also within the mixer-extruder 60. Continuous mixing is preferred to batch mixing, since the viscosity of the mixture expelled at 62 builds rapidly with respect to time of mixing. The liquid components introduced into the mixer-extruder 60 are preferably chilled, e.g., to between about $-25°$ C. and $+20°$ C. This decreases the rate of viscosity increase within the freshly extruded material 62. It is preferred that the triethylene glycol and glycerin, when used as humectants, are chilled to about $-25°$ C. to about $+10°$ C. The mixer-extruder 60 and its contents are preferably chilled to between about $-5°$ C. to about $+10°$ C. At this temperature, about one minute is allowed to coat the initially fluid hydrogel 62 onto the removable liner sheet 30. The hydrogel 62 usually enters the coater at a temperature between about $-25°$ C. and $+20°$ C., and preferably from about $-15°$ C. to about $+5°$ C.

If a viscosity stabilizer such as $Mg(OAc)_2$ is used, it is added to the mixture being introduced into the mixer-extruder 60 to help reduce the rate at which viscosity increases within the freshly extruded material 62. The freshly mixed hydrogel flows downwardly at 62 onto the lower removable liner sheet 30 and passes beneath a knife blade 64 as the sheet 30 is unrolled from a stock roll 30a and is carried to the right as seen in FIG. 10 by means of a conveyor 66, thereby advancing the freshly formed hydrogel sheet 14 toward the right in the figure beneath a heater 68 which can be used to heat the sheet 14 slightly, e.g., to about 100° F., to help set its structure.

Refer now to FIG. 11 which illustrates the forming of a composite couplant device 10. As seen in FIG. 11, the hydrogel sheet 14 is carried from left to right along with the lower liner sheet 30 by means of a conveyor (not shown) beneath a rotary cutter 70 which has rectangular cutting heads 72 that sequentially engage the continuous strip of hydrogel sheet material 14, thereby cutting it into rectangular pieces 14 shown at the right in the figure. The foam borders or frames 29 are then dropped down from above onto the patches of hydrogel sheet 14 so as to surround each successive patch of hydrogel material 14 as it moves toward the right in the figure. Finally, the upper removable liner sheet 12 formed, for example, from either a 5 mil layer of polyethylene or a sheet of siliconized paper is applied to the top of the composite device and the resulting structure is then cut into pieces by means of a reciprocating knife blade 74 or, in the alternative, rolled into a coil for shipment and storage prior to use.

Typical formulations for the hydrogel couplant sheet are shown in the following examples.

|  | Optimum Weight Range As A % by Weight of the Hydrogel Sheet | Typical (%) |
| --- | --- | --- |
| Example 1 | | |
| Polyacrylamide | 10–40 | 10 |
| Triethylene Glycol | 10–50 | 15 |
| Glycerin | 10–50 | 12.5 |
| Water | 10–70 | 60 |
| Mg(OAc)$_2$ | 1–12 | 2.5 |
| Example 2 | | |
| Polyacrylamide | 10–40 | 12 |
| Glycerin | 10–50 | 30 |
| Water | 10–70 | 55 |
| Mg(OAc)$_2$ | 1–12 | 3 |
| Example 3 | | |
| Polyacrylamide | 10–40 | 15 |
| Triethylene Glycol | 10–50 | 20 |
| Glycerin | 10–50 | 15 |
| Water | 10–70 | 50 |
| Example 4 | | |
| Polyacrylamide | 10–30 | 10 |
| Karaya | 5–15 | 5 |
| Triethylene Glycol | 10–50 | 15 |
| Glycerin | 10–50 | 12.5 |
| Citric Acid | 1–5 | 1.5 |
| SnCl$_2$ | .1–2 | 1.0 |
| Water | 1–70 | 60 |
| Example 5 | | |
| Polyacrylamide | 5–40 | 5 |
| Karaya | 5–15 | 10 |
| Triethylene Glycol | 10–40 | 15 |
| Glycerin | 10–40 | 15 |
| Water | 1–70 | 55 |
| Example 6 | | |
| Polyacrylamide | 10–30 | 15 |
| Maltodextrin (a partially hydrolized starch)* | 5–15 | 10 |
| Glycerin | 20–60 | 50 |
| Water | 1–70 | 18 |
| Mg(OAc)$_2$ | 1–12 | 1 |
| NaCl | 1–20 | 6 |
| Example 7 | | |
| Polyacrylamide | 10–40 | 10 |
| Triethylene Glycol | 10–50 | 15 |
| Glycerin | 10–50 | 12.5 |
| Water | 1–70 | 60 |
| Mg(OAc)$_2$ | 1–12 | 1.5 |
| NaCl | 1–20 | 1.0 |

*Lodex 10 ® by American Maize Products Company of Hammond, Indiana

Many variations of the present invention within the scope of the appended claims will be apparent to those skilled in the art once the principles described herein are understood.

What is claimed is:

1. A solid ultrasonic biomedical couplant in sheet form, comprising:

a hydrogel couplant sheet having a broad upper surface that is exposed to the air during use for receiving ultrasonic waves from a moveable ultrasonic generator such that the exposed upper surface allows direct contact between the generator and the hydrogel sheet, said sheet has a broad lower surface for being placed against the skin of a patient and for transmitting the ultrasonic waves through the skin interface to and from the body of the patient, the hydrogel sheet is adapted to extend over an area that includes different positions where readings are taken with the ultrasonic generator such that said ultrasonic generator is moveable to said different positions while in direct contact with said broad upper surface of the hydrogel sheet, said sheet comprising a dispersion of a natural or synthetic hydrophilic polymer, water and a humectant, said sheet is an integral self-supporting solid body of material having a defined shape in which the upper surface is a top portion of the solid body, the lower surface forms a bottom portion of the solid body, and an edge defines a periphery of the solid body, and said sheet is flexible and sufficiently pliant to conform to the body contours of the patient, the exposed upper surface of the hydrogel sheet has lubricating properties and the lubricity of the hydrogel sheet facilitates movement of the ultrasonic generator thereacross while the solid body of gel material remains in place on the skin of the patient as the generator is moved thereon, and means for holding the sheet against the skin of the patient to facilitate the transfer of ultrasonic waves generated by the ultrasonic generator to and from the body of said patient through different portions of the sheet.

2. The couplant sheet of claim 1 wherein the couplant sheet has a perimeter and a border formed from flexible sheet material encircles said hydrogel sheet to enclose said perimeter of the hydrogel sheet.

3. The couplant sheet of claim 2 wherein said border is formed from a flexible sheet of plastic or rubber foam having an adhesive layer on a lower surface thereof for bonding said sheet of foam to the skin of the patient.

4. A solid ultrasonic biomedical couplant in sheet form, comprising:

a hydrogel couplant sheet having a broad upper surface for receiving ultrasonic waves from an ultrasonic generator and a broad lower surface adapted to be placed against the skin of a patient and for transmitting the ultrasonic waves through the skin interface to and from the body of the patient, said sheet comprising a dispersion of a natural or synthetic hydrophilic polymer, water and a humectant, said sheet being flexible, solid and sufficiently pliant to conform to the body contours of the patient, means for holding the sheet against the skin of the patient to facilitate the transfer of said ultrasonic waves generated by said ultrasonic generator to and from the body of said patient through the sheet, a removable liner sheet is secured to at least one of said broad surfaces of said couplant sheet, and a selected portion of said liner sheet secured to said couplant hydrogel sheet is removably connected to the couplant hydrogel sheet and at least a portion of the liner sheet remains bonded to the hydrogel sheet following the removal of said selected portion of the liner sheet.

5. The couplant sheet of claim 4 wherein said hydrogel sheet has a tacky lower surface adapted to form a removable adhesive bond to the skin of the patient for holding the sheet against the skin of the patient during use but permitting the removal of the sheet by peeling the sheet away from the skin following use.

6. The couplant of claim 4 wherein the sheet has a peripheral border member and the portion of the liner sheet that remains bonded to the hydrogel sheet is also bonded to the border member.

7. A solid ultrasonic biomedical couplant in sheet form, comprising:

a hydrogel couplant sheet having a broad upper surface for receiving ultrasonic waves from an ultrasonic generator and a broad lower surface adapted to be placed against the skin of a patient and for transmitting the ultrasonic waves through the skin interface to and from the body of the patient, said sheet comprising a dispersion of a natural or synthetic hydrophilic polymer, water and a humectant, said sheet being flexible, solid and sufficiently pliant to conform to the body contours of the patient, means for holding the sheet against the skin of the patient to facilitate the transfer of said ultrasonic waves generated by said ultrasonic generator to and from the body of said patient through the sheet, said hydrogel includes a gelation inhibitor uniformly distributed therethrough in an amount sufficient to retard gelation of the hydrogel prior to forming the hydrogel into said flexible sheet.

8. The couplant sheet of claim 7 wherein a removable liner sheet is secured to at least one of said broad surfaces of said couplant sheet.

9. The couplant sheet of claim 8 wherein the liner sheet is one of paper or plastic film.

10. The couplant sheet of claim 7 wherein the gelation inhibitor comprises $Mg(OAc)_2$.

11. The couplant sheet of claim 7 wherein the polymer is at least one of the following: polyacrylamide, karaya or modified starch.

12. The couplant sheet of claim 7 wherein the humectant comprises at least one of the following: triethylene glycol, glycerin or propylene glycol.

13. The couplant sheet of claim 7 wherein a pressure-sensitive sheet is provided at a periphery of said hydrogel sheet in a position to surround said hydrogel sheet adapted to bond said hydrogel sheet to the skin and to seal at least the edge of the hydrogel sheet from the environment.

14. The couplant of claim 7 wherein the gelation inhibitor is a salt of a weak acid.

15. A solid ultrasonic biomedical couplant in sheet form, comprising:

a hydrogel couplant sheet having an upper surface for receiving ultrasonic waves from a moveable ultrasonic generator and a lower surface for being placed against the skin of a patient and for transmitting the ultrasonic waves through the skin interface to and from the body of the patient, the hydrogel sheet is adapted to extend over an area that includes different positions where readings are to be taken so that said ultrasonic generator is moveable to said different positions across the hydrogel sheet by being slid while being pressed toward the sheet, said sheet comprising a dispersion of a natural or synthetic hydrophilic polymer, water and a humectant, said sheet being flexible, solid and sufficiently pliant to conform to the body contours of the patient, the sheet is sized to allow movement of the ultrasonic generator thereacross, means for holding the sheet against the skin of a patient to facilitate the transfer of ultrasonic waves generated by the ultrasonic generator to and from the body of said patient through different portions of the sheet when the generator is moved to said different portions thereon, said hydrogel sheet is surrounded by a flexible border and said flexible border comprises a sheet of plastic or rubber, and said border has upper and lower surfaces and both said upper and lower surfaces have a layer of adhesive thereon.

16. A solid ultrasonic biomedical couplant in sheet form, comprising:

a hydrogel couplant sheet having a broad upper surface for receiving ultrasonic waves from an ultrasonic generator and a broad lower surface adapted to be placed against the skin of a patient and for transmitting the ultrasonic waves through the skin interface to and from the body of the patient, said sheet comprising a dispersion of a natural or synthetic hydrophilic polymer, water and a humectant, said sheet being flexible, solid and sufficiently pliant to conform to the body contours of the patient, means for holding the sheet against the skin of the patient to facilitate the transfer of said ultrasonic waves generated by said ultrasonic generator to and from the body of said patient through the sheet, said hydrogel sheet is surrounded by a flexible border and said flexible border comprises a sheet of foamed plastic or a foamed rubber, said border has upper and lower surfaces and at least said lower surface has a layer of adhesive thereon, and the upper and lower surface of the hydrogel sheet and the upper and lower surfaces of the surrounding border each have a liner sheet bonded thereto to thereby enclose the hydrogel sheet on all sides and at least the liner sheet that is bonded to the lower surface of the hydrogel sheet is removably bonded to the hydrogel sheet.

17. A method of performing ultrasonic diagnostics on the body of a patient by means of an ultrasonic transducer, comprising:

providing a hydrogel sheet having a broad upper surface for receiving ultrasonic waves from the ultrasonic transducer and a broad lower surface adapted to placed against the skin of the patient and for transmitting the sonic waves through the skin interface to the body of the patient, said hydrogel sheet comprising a dispersion of a natural or synthetic hydrophilic polymer, water and a humectant, said sheet is sufficiently pliant to conform to the body contours of the patient, the hydrogel sheet is adapted to extend over an area where readings are to be taken at different locations on the patient so that said ultrasonic transducer is moveable on said broad upper surface of the hydrogel sheet to multiple positions where said readings are to be taken, applying said hydrogel sheet to the skin of a patient, moving the transducer to different positions on the hydrogel sheet, transmitting ultrasonic wave energy from said instrument through different portions of the hydrogel sheet into the body of the patient, and receiving reflected ultrasonic energy from the body of the patient through the hydrogel sheet.

18. The method of claim 17 including, attaching a removable liner sheet to at least one of the surfaces of said hydrogel sheet, and removing said removable liner sheet prior to applying the hydrogel sheet to the skin of a patient.

19. The method of claim 17 including, providing a flexible border sheet surrounding said hydrogel sheet, and applying said hydrogel sheet and said flexible border sheet to the skin of the patient with the border sheet surrounding said hydrogel sheet.

20. The method of claim 17 including, providing a pressure-sensitive adhesive layer around the periphery of the hydrogel sheet, and bonding said pressure-sensitive adhesive layer around the periphery of said hydrogel sheet to the skin of the patient to aid in bonding said hydrogel sheet to the skin of the patient and to seal a peripheral portion of said hydrogel sheet from the atmosphere.

21. The method of claim 17 including, applying the hydrogel sheet to the skin by laying it or pressing it against the skin, providing the hydrogel sheet with a tacky lower surface wherein the tacky lower surface of the hydrogel sheet forms an adhesive bond with the skin.

22. A solid ultrasonic biomedical couplant in sheet form, comprising:

a hydrogel couplant sheet having a broad upper surface for receiving ultrasonic waves from an ultrasonic generator and a broad lower surface adapted to be placed against the skin of a patient and for transmitting the ultrasonic waves through the skin interface to and from the body of the patient, said sheet comprising a dispersion of a natural or synthetic hydrophilic polymer, water and a humectant, said sheet being flexible, solid and sufficiently pliant to conform to the body contours of the patient, means for holding the sheet against the skin of the patient to facilitate the transfer of said ultrasonic waves generated by said ultrasonic generator to and from the body of said patient through the sheet, a piece of cloth embedded within said hydrogel sheet for strengthening said sheet.

23. The couplant sheet of claim 22 wherein said hydrogel sheet is surrounded by a flexible border and said flexible border comprises a sheet of foamed plastic or a foamed rubber.

* * * * *